United States Patent [19]

Tsumura et al.

[11] Patent Number: 5,068,357

[45] Date of Patent: Nov. 26, 1991

[54] AN IMPROVEMENT IN THE PREPARATION OF N-SUBSTITUTED MALEIMIDES BY USE OF TIN CATALYSTS

[75] Inventors: Ryuichiro Tsumura; Teruo Muraishi, both of Yokohama; Keiichi Ideda, Chigasaki; Jin-Kai Wang, Yokohama, all of Japan

[73] Assignee: Mitsui Toatsu Chemicals, Inc., Tokyo, Japan

[21] Appl. No.: 536,366

[22] Filed: Jun. 11, 1990

[30] Foreign Application Priority Data

Jun. 16, 1989 [JP] Japan ................................. 1-152432
Apr. 26, 1990 [JP] Japan ................................. 2-108769

[51] Int. Cl.$^5$ .................. C07D 207/42; C07D 403/06; C07D 403/10; C07D 403/12
[52] U.S. Cl. .................................... 548/548; 548/521
[58] Field of Search ............................ 548/548, 521

[56] References Cited

FOREIGN PATENT DOCUMENTS

| 0165574 | 12/1985 | European Pat. Off. ............ 548/548 |
| 51-40078 | 11/1976 | Japan . |
| 55-46394 | 11/1980 | Japan . |
| 60-11465 | 1/1985 | Japan . |
| 61-60647 | 3/1986 | Japan . |
| 62-63562 | 3/1987 | Japan . |

*Primary Examiner*—David B. Springer
*Attorney, Agent, or Firm*—Millen, White & Zelano

[57] ABSTRACT

A process for the preparation of N-substituted maleimides by conducting heat-dehydration and dehydrating imidization of N-substituted maleamic acids under azeotropic distillation of generated water in a solvent mixture containing a solvent capable of forming water azeotrope and an organic aproptic polar solvent, in the presence as catalyst of metallic tin, tin oxide, a tin salt of a maleamic acid or a tin compound which forms a thin salt of the N-substituted maleamic acid in the reaction system.

20 Claims, No Drawings

AN IMPROVEMENT IN THE PREPARATION OF N-SUBSTITUTED MALEIMIDES BY USE OF TIN CATALYSTS

BACKGROUND OF THE INVENTION

1. Field of the Invention

The present invention relates to a process for the preparation of N-substituted maleimides.

2. Prior Art of the Invention

Various processes have traditionally been employed for preparing an N-substituted maleimide. In a generally known preparation process, maleic anhydride is reacted with a primary amine and the resulting N-substituted maleamic acid is imidized by cyclodehydration.

For example, N-phenyl maleimide can be prepared by an imidizing reaction through intramolecular cyclodehydration as follows:

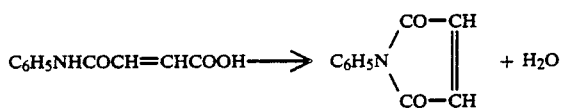

These processes can be roughly divided into those using a dehydrating agent and those using a catalyst.

The method which uses a dehydrating agent carries out the reaction by employing an equimolar amount or more of a dehydrating agent such as acetic anhydride as disclosed, for example, in U.S. Pat. No. 244,453 or Organic Syntheses, 41, 93. The method is excellent with respect to mild reaction conditions and relatively high yield of the reaction product. However, the method requires a large amount of expensive dehydrating agent and a complex treatment for separating the product after finishing the reaction. Consequently, the method leads to high production cost of the maleimide and is unsuitable for commercial production.

The dehydrating imidization method which uses a catalyst does not use a large amount of expensive auxiliary materials and is essentially an excellent economical method. The dehydrating reaction can occur merely by heating the maleamic acid in the presence of a solvent and the desired product maleimide is formed to some extent when heating is continued to remove the water of reaction from the reaction system. However, the rate of formation is too slow and impractical. Moreover, various unfavorable side reactions also occur and lead to lower selectivity. Accordingly, a catalyst is required for accelerating the dehydrating reaction and improving conversion and selectivity.

As a method using a catalyst, Japanese Patent Publication 51-40078 (1976) discloses a method for carrying out the imidization by dehydrating the maleamic acid in the presence of an acid catalyst and performing intramolecular cyclization by azeotropic distillation of the resulting water. The acid catalysts used are inorganic acids, such as sulfuric acid and phosphoric acid, and strong organic acids, such as p-toluenesulfonic acid having pka of 3 or less. Japanese Patent Publication 55-46394 (1980) describes a method using a solvent system obtained by incorporation of an aprotic polar solvent with an azeotropic solvent in order to enhance the solubility of the maleamic acid. There are also known methods, such as Japanese Patent Laid-Open No. 60-11465 (1985), which use strong acid type ion exchange resin as an acid catalyst and a method for directly obtaining the maleimide by reacting maleic anhydride with primary amine in the presence of the strong acid catalyst mentioned above. Other methods employ the acid catalyst in combination with various additives. For example, Japanese Patent Publication 51-40078 (1976) carries out the reaction by the addition of a stabilizer such as a polymerization inhibitor and an alcohol in the presence of the acid catalyst. Japanese Patent Laid-Open Nos. 61-5066 (1986) and 62-63562 (1987) conduct the reaction in the presence of such a strong acid catalyst as sulfuric acid or phosphoric acid by incorporating one or more metal compounds of zinc, chromium, cobalt, nickel, iron, aluminum or palladium in a trace amount of 0.005 to 0.5%, preferably 0.01 to 0.1% by mole per mole of aniline.

Japanese Patent Laid-Open No. 61-60647 (1986) reacts maleic anhydride with primary amine in an organic solvent to obtain a maleamic acid slurry and then intermittently or continuously charges the slurry to a second reaction vessel where the organic solvent is refluxing in the presence or absence of a catalyst. The catalyst is claimed as follows: "The suitable catalyst used is an oxyacid containing phosphorus or sulfur, or an alkaline metal salt or an alkaline earth metal salt thereof. In addition, salts, hydroxides, oxides and halides of the same metals (Ni, Co, Cu, Zn, Sn, Al, B, Sb, Li, Mg, Cr, Ti, V, Mn and Fe) as those of catalysts usually used for esterification, or a montmorillonite catalyst can also be used as a catalyst." In the detailed specification disclosed as exemplary catalysts are many kinds of strong acids, and sodium salts and magunesium salts thereof. However, no description is given of a specific metal compound as the catalyst, but the above claim is only described again about metal compounds. Some kinds of acid catalysts are used in the examples, but no example is disclosed which uses such metal compounds. Since the above patent application has merely claimed many metal compounds, in addition to the acid catalyst, as a dehydrating imidization catalyst without any technical disclosure and, moreover, by wrong understanding as mentioned hereafter, it is not recognized at all as the so-called prior art in the aspect of metal-catalyzed reactions.

The common essential element for these known methods of catalytically dehydrating imidization is the use of an acid catalyst having strong Broensted acidity, for example, inorganic protic acids, such as sulfuric acid, phosphoric acid, hydrobromic acid and fluorosulfonic acid, and organic protic acids, such as chloroacetic acid, fluoroacetic acid, trifluoromethanesulfonic acid, p-toluenesulfonic acid and sulfonic acid type ion exchange resins.

The process for preparing the N-substituted maleimide by catalytically conducting dehydrating imidization of the N-substituted maleamic acid is a direct reaction which does not consume auxiliary materials and hence is a substantially economical process. Accordingly, many acid-catalyzed methods are known, as mentioned above. However, none have been technically or economically satisfactory for commercial production of the N-substituted maleimides.

SUMMARY OF THE INVENTION

An object of the present invention is to provide a process for the preparation of a maleimide by a novel dehydrating imidization process which does not require the use of an acid catalyst.

Another object of the present invention is to provide a novel process which has substantially solved the important technical problems associated with the use of an acid catalyst, such as:

(1) poor selectivity or insufficient yield even though the above known inorganic or organic strong acid is used, (2) an inorganic acid or an expensive organic acid used as the catalyst in a large amount is poor in separating ability against an organic phase and hence is difficult to separate and recover after finishing the reaction, (3) the acid catalyst is apt to contaminate the reaction product and also has relatively low selectivity and hence leads to contaimination of the desired product with a large amount of by-products, which circumstances require complex purification procedures such as washing with water and separation in order to remove these impurities from the product, (4) the washing with water produces a large amount of waste water which must be treated before disposal, and (5) a strong acid catalyst used in a large amount at high temperatures requires anticorrosive materials for reactors and peripheral equipment, and hence leads to expensive production units.

An object of the present invention is to solve these problems and to provide an economical large scale production process which can prepare an N-substituted maleimide from an N-substituted maleamic acid in high yield.

The process of the present invention can economically prepare an N-substituted maleimide with high selectivity and in good yield from maleic anhydride or a derivative thereof and a corresponding primary amine or from the corresponding N-substituted maleamic acid.

High purity maleimide which is particularly useful for a material of polymers can be readily produced on a large scale by the process of the present invention.

The present invention relates to a process for the preparation of an N-substituted maleimide by heat-dehydrating an N-substituted maleamic acid in a solvent mixture containing an organic solvent capable of forming water azeotrope and an organic aprotic polar solvent and simultaneously conducting a dehydrating imidization reaction under azeotropic distillation of the reaction generated water, which comprises conducting the dehydrating imidization in the absence of an acid catalyst and in the presence as reaction catalyst of a catalytically effective amount of metallic tin, tin oxide, a tin salt of the maleamic acid, a tin compound which forms a tin salt of the maleamic acid in the reaction system, or mixtures thereof.

DETAILED DESCRIPTION OF THE INVENTION

Previously, the present inventors considered the need for developing a novel and practical catalyst having high selectivity capable of replacing the conventional acid catalyst in order to substantially overcome the above problems.

As a result of various experiments on the catalyst, they found that dehydrating imidization can be suitably conducted without using the above mentioned acid catalysts and merely by adding a catalytically effective amount of a zinc salt of the maleamic acid, metallic zinc or a compound capable of forming said salt in the reaction system. A patent application was filed prior to the present invention (Japanese Patent Application HEI 1-30764(1989)).

In the reaction using a zinc catalyst such as zinc powder or zinc acetate, the inventors succeeded in isolating novel zinc salts of the maleamic acid. Separately, said zinc salts were synthesized by another preparative method and applied as catalysts to the same dehydrating imidization in a catalytic amount, resulting in high yield of maleimides. It was further confirmed that the zinc salt was a precursor of the catalyticly active species in the reaction.

As a result of the detailed research on the reaction mechanism, a zinc-coordinated catalysis was presumed that an N-substituted maleamic acid is coordinately activated by forming said salt with zinc so as to sterically undergo intramolecular cycloimidization with ease and, on heating, dehydrated to give an N-substituted maleimide rapidly and selectively.

In order to further improve the performance of the catalyst on the basis of the above assumption, a great deal of experiments has been carried out on various metals and metal compounds. As a result, it has been surprisingly found that practically useful results which are suitable for the above objects and superior to the zinc catalyst can be obtained by conducting the dehydrating imidization reaction in the absence of an acid catalyst and in the presence of a catalytic amount of metallic tin, tin oxide, a tin salt of the maleamic acid and/or a tin compound capable of forming said tin salt in the reaction system. Thus the present invention has been completed (Japanese Patent Applications HEI 1-152432(1989) and HEI 2-108769(1990)).

In a similar manner to the zinc catalyst, the inventors succeeded in separating and identifying novel tin salts of the maleamic acid in the imidization reaction using a tin catalyst such as stannous oxide or stannous acetate. Separately, said tin salts were prepared by another method and proved to be highly active and selective catalysts in the dehydrating imidization as indicated in Examples. They were confirmed to be the socalled precursors of the catalytically active intermediates which promoted the intramolecular cycloimidization more selectively than the zinc catalysts.

Because strong, e.g., pKa 3 or lower, Broensted acids interfere with or prevent the formation of the tin salt of the maleamic acid or decompose the salt if added to the reaction mixture as the catalyst, the process of the present invention is conducted in the absence of such strongly acidic compounds.

As to the metal compound used for the esterification catalyst in the above Japanese Patent Laid-Open No. 61-60647 (1986), as illustrated in Comparative Examples, most of these metal compounds, for example, Ni, Co, Cu, B, Mg, Cr, Mn and Fe, are inactive as catalysts for the reaction of the present invention or exhibit no improvement in selectivity. Hence no common feature in catalysis can be found at all between the esterification reaction and the dehydrating imidization reaction of the present invention.

The N-substituted maleamic acid used as starting material for the process of the present invention is an N-substituted monomaleamic acid, preferably one represented by formula (I):

RaNHCOCRd=CReCOOH  (I)

wherein Ra is a monovalent radical, e.g., of an aliphatic, alicyclic or aromatic group of from 1 to 30 carbon atoms, and Rd and Re, which may be the same or different, are hydrogen atoms or monovalent substituents which are inactive under the reactions, or an N-substituted bis- and poly-maleamic acid represented by formula (II) or (III):

Rb(NHCOCRd=CReCOOH)₂ (II)

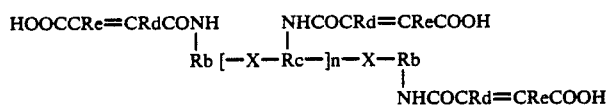
(III)

wherein Rb is a divalent radical, e.g., of an aliphatic, alicyclic or aromatic group having from 1 to 30 carbon atoms, Rc is a trivalent radical, e.g., of an aliphatic, alicyclic or aromatic group having from 1 to 30 carbon atoms, X is a divalent substituent which is inactive under the reaction conditions, and n is an integer of 0 to 50.

The starting N-substituted maleamic acids are compounds which can be readily obtained according to a known method in an almost theoretical yield by reacting a corresponding substituted or unsubstituted maleic anhydride with a primary mono-, di- or polyamine, preferably in a solvent.

Exemplary N-substituted mono-maleamic acids include, for example, compounds wherein Ra in the formula is an aliphatic group, e.g., methyl, ethyl, n-propyl, i-propyl, n-butyl, sec-butyl, tert-butyl, amyl, i-amyl, hexyl, octyl, 2-ethylhexyl, dodecyl, octadecyl, or a corresponding unsaturated group, e.g., allyl, or a corresponding group bearing an aryl substituent, e.g., benzyl; an alicyclic group, e.g., as cyclopentyl and cyclohexyl; or an aromatic group, e.g., phenyl, naphthyl, or a corresponding group bearing 1,2 or more substituents, such as alkyl, halo, nitro, hydroxy, alkoxy, aryloxy, aryloyl, hydroxycarbonyl etc., e.g., tolyl, xylyl, styryl, dodecylphenyl, benzylphenyl, chlorophenyl, dichlorophenyl, hydroxyphenyl, methoxyphenyl, phenoxyphenyl, benzoylphenyl, carboxyphenyl and nitrophenyl. Also included are maleamic acid compounds wherein Ra has one or more substituents inactive in the reaction of the present invention, for example, a halogen group, alkyl group, cycloalkyl group, aryl group, hydroxyl group, alkoxy group, aryloxy group, alkylmercapto group, nitro group, hydroxycarbonyl group, alkoxycarbonyl group, alkanoyl group, aryloyl group, nitrile group and a group containing monovalent substituents obtained by combining these groups.

Representative examples of Rd and Re substituents on the double bonded carbon atoms include, in addition to hydrogen atoms, the same monovalent substituents as described above for Ra.

Exemplary mono-maleamic acids which are particularly useful in the process of this invention includes, for example, N-methylmaleamic acid, N-butylmaleamic acid, N-octylmaleamic acid, N-dodecylmaleamic acid, N-stearylmaleamic acid, N-cyclohexylmaleamic acid, N-phenylmaleamic acid, N-(o-tolyl)maleamic acid, N-dodecylphenylmaleamic acid, N-chlorophenylmaleamic acid, N-dichlorophenylmaleamic acid, N-(o- or p-hydroxyphenyl)maleamic acid, N-(o- or p-methoxyphenyl)maleamic acid, N-(m-hydroxycarbonylphenyl)maleamic acid, and N-(m-nitrophenyl)maleamic acid.

Representative examples of N-substituted bis- and poly-maleamic acids include, for example, compounds of formulae (II) and (III) wherein Rb is a divalent bridging group, e.g., aliphatic group, such as ethylene, tetramethylene and hexamethylene; an alicyclic group such as cyclohexylene and methylenebis(cyclohexylene); and an aromatic group such as phenylene, tolylene, xylylene, styrylene, dodecylphenylene, naphthylene, chlorophenylene, dichlorophenylene, hydroxyphenylene, methoxyphenylene, phenoxyphenylene, benzoylphenylene, carboxyphenylene and nitrophenylene. Rb also includes, as in the case of Ra, a group containing the above monovalent substituents which are inactive in the reaction.

X in formula (III) is a divalent substituent, including, for example, alkylene groups, such as methylene, dimethylmethylene, cyclohexylmethylene, phenylmethylene, ethylene, propylene, tetramethylene and hexamethylene; the same divalent alicyclic groups as Rb, e.g., cyclohexylene; divalent aromatic groups such as phenylene, tolylene and xylylene; ether groups; ketone groups; ester groups; amide groups; disulfide groups; sulfone groups; —O(C₆H₄)O—; —O(C₆H₄)CO(C₆H₄)O— and —O(C₆H₄)SO₂(C₆H₄)O—. These divalent substituents also include, as in the case of Ra, a group containing the above monovalent substituents which are inactive in the reaction.

Rc includes, for example, trivalent benzene ring substituents (C₆H₃) and also, as in the case of Ra, a group wherein hydrogen atoms are replaced with the above monovalent substituents which are inactive in the reaction. When n is zero in formula (III), the formula indicates bis-maleamic acid. Wherein n is 1 or more, the formula indicates oligo- or poly-maleamic acid.

Exemplary N-substituted bis-maleamic acids particularly useful for the practice of the present invention include, for example,
N,N'-(m- or p-phenylene)bis-maleamic acid,
N,N'-(2,4-tolylene)bis-maleamic acid,
N,N'-(4,4'-diphenylmethane)bis-maleamic acid,
N,N'-(4,4'-diphenylether)bis-maleamic acid,
N,N'-(4,4'-diphenylketone)bis-maleamic acid,
N,N'-(4,4'-diphenyldisulfide)bis-maleamic acid and
N,N'-(4,4'-diphenylsulfone)bis-maleamic acid.

Additionally, N,N'-(4,4'-p-xylylenediphenyl)bis-maleamic acid having the structure wherein Rb is a phenylene group, X is a xylylene group, Rd and Re are hydrogen atoms, and n is zero in formula (III), can also be used for the practice of the invention.

Particularly useful examples of N-substituted polymaleamic acids include, for example, polymethylenepolyphenylenepolymaleamic acid having the structure in the formula (III) [a polymeric homologue of N,N'-(4,4'-diphenylmethane)bis-maleamic acid] wherein Rb and Rc are benzene rings, X is a methylene group, Rd and Re are hydrogen atoms, and n is an integer of 1 to 10; and an aromatic polymaleamic acid having the structure [a polymeric homologue of N,N'-(4,4'-p-xylylenediphenyl)bis-maleamic acid] wherein Rb and Rc are benzene rings, X is a xylylene group, Rd and Re are hydrogen atoms and n is an integer of 1 to 10.

In the process of the present invention a maleamic acid can be prepared in a solvent from maleic anhydride or its substituted derivertive and a primary amine, and the dehydration reaction conducted using the resultant maleamic acid as such without isolation.

The mole ratio of maleic anhydride to the amino group in the primary amine employed preferably is stoichiometric. However, it is often preferred to use a slight excess of maleic anhydride, for example, in the range of about 1 to 1.1 by mole ratio. The excess maleic anhydride can be recovered after the finish of reaction and used again.

The present invention is carried out by using tin catalyst in the absence of an acid catalyst.

The catalyst for use in the process of the present invention is one or more of tin components selected from the group consisting of metallic tin, tin oxide, a tin salt of maleamic acid, and a tin compound capable of forming said maleamic acid tin salt in the reaction system.

The acid catalyst is a known catalyst having a strong Broensted acidity as stated above. Representative examples of the acid catalyst include inorganic protic acids such as sulfuric acids, phosphoric acid, hydrobromic acid, and fluorosulfonic acid; and organic protic acids such as chloroacetic acid, fluoroacetic acid, trifluoromethanesulfonic acid, p-toluenesulfonic acid and sulfon type ion exchange resin.

These acid catalysts inhibit formation of the tin salt of maleamic acid. Consequently, in the presence of the acid catalyst, the catalytic reaction of tin in the present invention is inhibited.

First of all, metallic tin and tin oxide are used as the catalyst and form maleamic acid salts in the reaction system.

No particular restriction is imposed upon the form of metallic tin and fine powder of tin is preferred.

Tin oxide used is stannous oxide SnO or tin oxide containing divalent tin atom. Stannous oxide, tin (II) oxide composed of divalent tin atom, effectively functions in the catalytic reaction of the invention. On the other hand, stannic oxide, tin (IV) oxide composed of tetravalent tin atom, is quite catalytically inactive as illustrated in the comparative example below but does not interfere with the reaction. Tin (II) oxide undergoes disproportionation into tin and tin (IV) oxide on heating to form many intermediate oxides such as $Sn_2O_3$, $Sn_3O_4$ and $Sn_5O_6$ between SnO and $SnO_2$. Any tin oxide can also be used as the catalyst of the invention so long as it contains divalent tin atom in the composition.

Tin salt of maleamic acid is a tin salt containing the above maleamic acid and also includes the corresponding tin salt adduct obtained by coordinating with an organic or inorganic neutral ligand or water of crystallization.

The N-substituted maleamic acid used as a component of the catalyst may be the same as or different from that used as a starting material for the dehydration reaction but preferably is the same. The ligand is an organic or inorganic ligand capable of coordinating nonionic atoms such as nitrogen, oxygen and phosphorus to tin. Exemplary ligands include, for example, amines, amides, alcohols, esters, ethers, phosphines, phosphites and water. Representative examples of preferred ligands are ligands of the polar solvents of the present invention described below or water of crystallization. The tin salt of maleamic acid containing no ligand at all can also be used.

Tin salts of monomaleamic acids are very important as a precursor for the active catalyst in the reaction of the present invention. Since a polymaleamic acid is also used as a starting material, the tin salts are not limited to those of monomaleamic acids. Thus, the tin salts useful as the catalyst can generally be defined as a compound represented by the formula (IV):

$$Sn(OCORe=CRdCONHRa)^{+m} \qquad (IV)$$

wherein m is 1 or 3. Each tin atom bears at least one maleamic acid group.

Exemplary catalysts suitable for use in the process of the invention includes, for example, the tin salts of N-methylmaleamic acid, N-butylmaleamic acid, N-dodecylmaleamic acid, N-stearylmaleamic acid, N-cyclohexylmaleamic acid, N-phenylmaleamic acid, N-tolylmaleamic acid, N-chlorophenylmaleamic acid, N-nitrophenymaleamic acid and N-hydroxyphenylmaleamic acid, and the corresponding tin salt adduct obtained by coordinating a neutral ligand or water of crystallization to the tin salt. Other examples are tin salts of N,N'-(m- or p-phenylene)bis-maleamic acid, N,N'-(2,4-tolylene)bis-maleamic acid, N,N'-(4,4'-diphenylmethane)bis-maleamic acid, N,N'-(4,4'-diphenylether)bis-maleamic acid, N,N'(4,4'-p-xylylenediphenyl)bis-maleamic acid and a tin salt adduct thereof similar to the above.

Further, various tin compounds can be used for the in situ production of the catalyst which are capable of forming one of the above described maleamic acid tin salts in the reaction mixture. No particular limitation other than their ability to form a maleamic acid salt in situ, is imposed upon such tin compounds, which include, for example, organic carboxylic acid salts and halides of divalent or tetravalent tin.

Tin salts of carboxylic acids suitable for use as the catalyst include salts of weak monovalent and polyvalent aliphatic, alicyclic and aromatic carboxylic acids having a pKa above 3. Representative examples of carboxylic acids which may be used include, for example, acetic acid, propionic acid, butyric acid, 2-ethylhexanoic acid, octanoic acid, lauric acid, stearic acid, glycine, lactic acid, succinic acid, glutaric acid, adipic acid, azelaic acid, maleic acid, fumaric acid, citric acid, cyclohexylcarboxylic acid, naphthenic acid, benzoic acid, tolylic acid, chlorobenzoic acid, phthalic acid and terephthalic acid. Particularly preferred acids are acetic acid, 2-ethylhexanoic acid, stearic acid, benzoic acid and naphthenic acid.

Tin halides are halogen containing tin compounds such as stannous chloride, stannic chloride, stannous bromide, stannic bromide, stannous iodide, stannic iodide and dichloro tin bisacetylacetonate. Stannous chloride and stannic chloride are preferably used.

The above-described catalyst is generally used singly but may be used as a mixture when desired.

Tin compounds in addition to those mentioned above can also be used so long as they form a catalyst containing maleamic acid of the invention.

No particular limitation is placed upon the amount of the catalyst used but the amount is usually in the range of 0.1 to 20 mole % (0.001 to 0.2 gram atom of tin), preferably in the range of 0.5 to 10 mole % (0.005 to 0.1 gram atom of tin) per mole of the maleamic acid starting material.

Similar to the optimum quantity of the solvent in commercial use, the amount of catalyst used depends upon the starting material, the solvent used and the reaction conditions employed. Known acid catalysts require recovery and reuse in view of the amount used.

A complex washing step is also inevitable in processes using known acid catalysts due to accompanied contamination of the product. In contradistinction, the process of the present invention is the first process using tin and/or its salt as the catalyst instead of an acid catalyst and the catalyst is readily separated after finishing the reaction. Recovery and recycle of the catalyst are carried out with ease. The product can be readily purified and a complex post treatment is not necessarily required.

As can be seen by comparing the below described examples of the present invention with the Comparative Examples, the catalyst of the invention prevents side reactions, such as hydrolysis of cyclic imide, addition to double bonds between carbon atoms and polymerization, in addition to accelerating the dehydrating imidization reaction. Consequently, the catalyst performs the excellent function of improving the selectivity of the reaction.

An organic solvent capable of forming water azeotrope is used in the present invention for removing water generated by the reaction by azeotropic distillation. The azeotropic solvent is one which forms water azeotrope preferably in the temperature range from 50° to 200° C. and is inert under the reaction conditions. Suitable solvents include, for example, cyclohexane, benzene, toluene, ethylbenzene, xylene, cumene, chlorobenzene, anisole, dichloroethane, diethoxyethane, cyclohexanone, methyl ethyl ketone, methyl i-buthyl ketone and trioxane. The preferred solvents are xylenes in view of their properties and cost.

The organic aprotic polar solvent is used for increasing the concentration of maleamic acid and the catalyst in the solution. Exemplary aprotic polar solvents suitable for the process of the present invention include dimethylformamide, dimethylacetamide, dimethylsulfoxide, sulfolane, methylisobutylketone, γ-butyrolactone hexamethylphosphoramide, N-methylpyrrolidone, tetramethylurea and 1,3-dimethyl-2-imidazolidinone. The preferred aprotic polar solvents are dimethylformamide, dimethylacetamide and dimethylsulfoxide.

These polar solvents generally decompose by heating in the presence of a strong acid and form reactive acids and amines. Thus, a conventional dehydrating imidization process which uses an acid catalyst decomposes the polar solvent in the course of reaction and the decomposition products further increase by-products of the dehydrating imidization. On the other hand, the tin catalyst of the present invention can prevent decomposition of the polar solvent. It is a commercially important characteristic of the present invention that decomposition of the solvent and accompanied decrease in the selectivity of maleimide product can be avoided.

The amount of the solvent mixture used is usually in an amount which provides a concentration of maleamic acid starting material therein to solvent in the range of 0.1 to 5 moles/l, preferably 0.5 to 3 moles/l. The content of polar solvent in the solvent mixture is usually in the range of 0.1 to 50% by volume and preferably in the range of 1 to 20% by volume. Optimum values of raw material concentration and solvent composition are dependent upon the starting material, catalyst, solvent and the reaction conditions such as catalyst amount, temperature and reaction time, employed.

Stabilizers such as known polymerization inhibitors may be added before the dehydrating reaction or in the separation and purification step after the finish of the reaction.

Exemplary stabilizers suitable for use include, for example, quinones such as hydroquinone, tert-butylhydroquinone and methoxybenzoquinone; phenols and bisphenols such as tert-butylcatechol and methoxyphenol; amines such as alkyldiphenylamine; sulfur compounds such as phenothiazine, mercaptobenzimidazol and methyleneblue; metal salts of dialkyldithiocarbamic acids such as copper dimethyldithiocarbamate and zinc dibutyldithiocarbamate; thiopropionic acid esters such as distearyl 3,3'-thiodipropionate; and phosphites such as triphenyl phosphite.

The reaction temperature employed is usually in the range of 50° to 200° C., and preferably is in the range of 80° to 160° C. In practice, optimum temperature depends upon the kind and composition of the above solvent mixture and concentration of the starting material. Although no particular restriction is imposed upon the reaction pressure, the reaction is preferably carried out under atmospheric pressure. Reaction time is usually in the range of 0.5 to 10 hours and preferably in the range of 1 to 5 hours, although optimum reaction time is practically determined on the basis of the selection of other reaction conditions.

The embodiments for preparing the maleimide from the maleamic acid by the process of the present invention will be illustrated below. The reaction can be carried out by batch, semicontinuous or continuous process.

Maleamic acid, the organic solvent for water azeotrope, organic aprotic polar solvent and the catalyst are mixed prior to reaction and charged to a reactor. Alternatively, maleamic acid and the catalyst are separately charged to the reactor together with the solvent respectively. The reactor is heated thereafter or in advance. The azeotropic solvent is heat-refluxed for a prescribed time and the generated water is simultaneously distilled out of the reactor as an azeotropic mixture. The reaction thus progresses and maleamic acid is converted to maleimide.

In the process of the present invention, it is unnecessary to prepare the maleamic acid starting raw material separately. Preferably, maleic anhydride or a derivative thereof is dissolved in the above azeotropic solvent or the mixture thereof with the polar solvent and the corresponding primary amine is added to the solution to prepare maleamic acid in situ. Then the catalyst is directly added to the maleamic acid solution or slurry thus obtained and the mixture is then refluxed to carry out the above azeotropic dehydration reaction. The maleamic acid can thus be prepared in an almost theoretical yield. Hence the latter process is usually more economical.

The reaction mixture thus obtained desirably is transferred to an evaporator to recover both solvents and then subjected to extraction, crystallization or distillation. The maleimide thus obtained has a purity of 90 to 100% and usually about 95 to 99.9%. The residue of extraction, crystallization or distillation contains by-products and the catalyst in addition to a small amount of maleimide and unreacted maleamic acid. The residue can be returned to the reaction system for reuse as such or after suitable treatment. The tin catalyst can also be separated by precipitation immediately after finishing the reaction or after separating the solvents, or by extracting from the solution.

The maleimide thus obtained can be readily converted to a high purity product suitable for practical application by usual purification methods such as extraction, crystallization, washing and distillation. Alternatively, maleimide can also be employed for commercial application as a solution in a suitable solvent when necessary.

The tin metal base catalyst employed in the present invention exhibits no corrosivity, which behavior is markedly different from that of the conventional strong acid catalysts. Consequently, conventional and inexpensive materials can be used for the equipment and production units.

As mentioned above, the novel tin catalyst employed in the present invention permits prepation of N-substituted maleimides, (1) in an extremely high selectivity and yield, (2) the catalyst can readily be separated, (3) without a complex purification step, such as washing with water, (4) without the expense of waste water disposal, and (5) using a reactor constructed with unexpensive conventional materials.

The present invention provides a process for economically preparing an N-substituted maleimide, in the presence of a high activity catalyst selected from the group consisting of metallic tin, tin oxide, a tin salt of maleamic acid and a tin compound capable of forming said tin salt of the maleamic acid in the reaction system, by using maleic anhydride or a substituted derivative thereof and a corresponding primary amine as starting materials or by using an N-substituted maleamic acid as a raw material, in extremely high selectivity and yield, using simple separation and purification procedures.

The maleimides are useful for a material of various resins, agricultural chemicals and medicines. Particularly in recent years, they are utilized in large amounts for improving heat resistance of styrene base resin and the application to a comonomer for modifying other resins and a copolymer for polymer blend is now under development.

The invention will be hereinafter illustrated further in detail by way of examples. However, it should of course be borne in mind that the subject matter and scope of the present invention are not limited by these examples.

EXAMPLE 1

To a 300 ml flask equipped with a water separator connected to reflux condenser, stirrer and a thermometer, 15.44 g of maleic anhydride (hereinafter abbreviated as MAN), 70 ml of xylene (hereinafter abbreviated as Xy) and 10 ml of dimethylformamide (hereinafter abbreviated as DMF) were charged. A mixture of 13.97 g of aniline (hereinafter abbreviated as AN) and 20 ml of xylene was added with stirring at 80° C. at a constant rate over 15 minutes and further aged for 15 minutes to obtain N-phenylmaleamic acid as a white slurry. To the slurry, 0.530 g (2.5% by mole per mole of MAN) of stannous oxide (hereinafter abbreviated as SnO) was added and the mixture was heated to reflux with stirring. Water generated by the reaction was removed by azeotropic distillation and the reaction was carried out at about 140° C. for 3.5 hours. The white slurry of PMA gradually dissolved as the dehydration reaction progressed and an orange yellow solution was obtained from which the catalyst component precipitated.

The solvent was recovered by evaporation under reduced pressure and the residue was extracted with hot cyclohexane. The extracted solution was successively concentrated to dryness to yield 22.88 g of extract, identified as N-phenylmaleimide (hereinafter abbreviated as PMI) by liquid chromatography, as yellow needles. The purity was 98.3% and content of PMA was 1.4%. The 3.88 g of extraction residue contained 15.6% of PMI, 42.9% of PMA and 1.8% of MAN.

The yields of PMI and PMA based on AN and selectivity of PMI based on PMA as an effective intermediate are summarized in Table 1, No. 1.

EXAMPLE 2

The procedure of Example 1 was employed except that twice by weight of the catalyst was used and the dehydration reaction was conducted for 2.5 hours. The results are illustrated in Table 1, No. 2.

EXAMPLE 3

The procedure of Example 1 was repeated except that 15.00 g of MAN and 0.505 g of the catalyst were used. The results are illustrated in Table 1, No. 3.

EXAMPLE 4

The procedure of Example 1 was repeated except that 22.06 g of MAN and 0.505 g of the catalyst were used. The results are illustrated in Table 1, No. 4.

EXAMPLE 5

The procedure of Example 1 was repeated except that 20.59 g of MAN, 18.63 g of AN and 0.673 g of the catalyst were used. The results are illustrated in Table 1, No. 5.

EXAMPLE 6

The procedure of Example 1 was repeated except that 30.89 g of MAN, 27.94 g of AN and 1.010 g of the catalyst were used. The results are illustrated in Table 1, No. 6.

EXAMPLES 7–9

The procedure of Example 1 was repeated except that ethylbenzene (abbreviated as PhEt in Table 1), chlorobenzene (abbreviated as PhCl in Table 1) and Cumene (abbreviated as Cum in Table 1) respectively were used instead of Xy. The results are illustrated in Table 1, Nos. 7–9.

EXAMPLES 10–12

The procedure of Example 1 was repeated except that 0.505 g of the catalyst was used and dimethylacetamide (hereinafter abbreviated as DMAC), dimethyl sulfoxide (hereinafter abbreviated as DMSO) and N-methylpyrrolidone (hereinafter abbreviated as NMP) respectively were used as the solvent instead of DMF. The results are illustrated in Table 1, Nos. 10–12.

EXAMPLE 13

To the same type of the 500 ml reactor used in Example 1, 76.48 g of PMA, 180 ml of Xy, 20 ml of DMF and 1.616 g of the catalyst were charged and heated to reflux. The reaction was carried out at about 140° C. for 3 hours by azeotropically distilling off the generated water. The white slurry of PMA gradually dissolved as the reaction progressed and an orange yellow solution was obtained from which the catalyst component precipitated. The reaction mixture was treated by the same procedures as carried out in Example 1. The results are illustrated in Table 1, No. 13.

EXAMPLE 14

To the same type of the 1 l reactor used in Example 1, 144.2 g of MAN and 630 ml of Xy were charged and then 130.4 g of AN was fed with vigorous stirring at 30° to 80° C. over one hour to yield PMA as a white slurry. To the slurry, 70 ml of DMF and 9.428 g of the catalyst were added and the mixture was submitted to the reactor and the separation by the same procedure as carried out in Example 1. The results are illustrated in Table 1, No. 14.

EXAMPLE 15

The procedure of Example 5 was repeated except that 1.347 g of tin oxide containing 75 weight % of SnO as the catalyst and DMAC instead of DMF were used. The results are illustrated in Table 1, No. 15.

EXAMPLES 16-18

The procedure of Example 1 was repeated except that 0.932 g of stannous acetate (abbreviated as $Sn(OAc)_2$ in Table 2 and 4), 1.669 g of stannous 2-ethylhexanoate containing 28 weight % of Sn (abbreviated as $Sn(OCOHep)_2$ in Table 2) and 1.421 g of stannous benzoate (abbreviated as $Sn(OCOPh)_2$ in Table 2) were respectively used. The results are illustrated in Table 2, Nos. 16-18.

EXAMPLES 19-21

The procedure of Example 1 was repeated except that 1.97 g of a novel stannous salt of N-phenylmaleamic acid (hereinafter abbreviated as $Sn(PMA)_2$) separated from the reaction mixture, 2.25 g of a novel DMF adduct of $Sn(PMA)_2$ (abbreviated as $Sn(PMA)_2.DMF$ in Table 2) and 2.36 g of a novel triethylamine adduct of $Sn(PMA)_2$ (abbreviated as $Sn(PMA)_2.TEA$ in Table 2) respectively were used as the catalyst instead of SnO, and reflux was carried out for 3 hours. The results are illustrated in Table 2, Nos. 19-21.

EXAMPLE 22

The procedure of Example 3 was repeated except that 1.811 g of stannous acetate was used as the catalyst. The results are illustrated in Table 2, No. 22.

EXAMPLE 23

The procedure of Example 5 was repeated except that 4.451 g of stannous 2-ethylhexanoate was used as the catalyst and refluxing was carried out for 2 hours. The results are illustrated in Table 2, No. 23.

EXAMPLE 24

The procedure of Example 6 was repeated except that 6.676 g of stannous 2-ethylhexanoate was used as the catalyst and reflux was carried out for 2 hours. The results are illustrated in Table 2, No. 24.

EXAMPLES 25 and 26

The procedure of Example 23 was repeated except that PhEt and PhCl were respectively used as the solvent instead of Xy, 2.225 g of the catalyst was charged and reflux was carried out for 3.5 hours. The results are illustrated in Table 2, Nos. 25 and 26.

EXAMPLES 27-29

The procedure of Example 23 was repeated except that DMAC, DMSO and NMP were respectively used as the polar solvent instead of DMF, 1.183 g of stannous acetate was charged as the catalyst and reflux was carried out for 3.5 hours. The results are illustrated in Table 2, Nos. 27-29.

EXAMPLE 30

The procedure of Example 23 was repeated except that PMA was prepared in 90 ml of Xy without addition of DMF, and then 10 ml of DMF together with 2.486 g of stannous acetate as the catalyst was added to the slurry of PMA in Xy. The results are illustrated in the Table 2, No. 30.

EXAMPLE 31

The procedure of Example 13 was repeated except that 2.841 g of stannous acetate was used as the catalyst and reflux was carried out for 3.5 hours. The results are illustrated in the Table 2, No. 31.

EXAMPLE 32

The procedure of Example 5 was repeated except that 0.623 g of metallic tin in fine powder was used as the catalyst instead of SnO. The results are illustrated in Table 3, No. 32.

EXAMPLES 33-36

The procedure of Example 1 was repeated except that 0.747 g of anhydrous stannous chloride (abbreviated as $SnCl_2$ in Table 3), 0.888 g of stannous chloride (abbreviated as $SnCl_2.2H_2O$ in Table 3), 1.03 g of anhydrous stannic chloride (abbreviated as $SnCl_4$ in Table 3) and 1.38 g of stannic chloride (abbreviated as $SnCl_4.5H_2O$) were respectively used as the catalyst instead of SnO. The results are illustrated in Table 3, Nos. 33-36.

EXAMPLE 37

To the same reactor used in Example 1, 15.44 g of MAN and 70 ml of Xy were charged. A mixture containing 16.3 g (0.15 mole) of p-aminophenol (hereinafter abbreviated as PAP), 65 ml of Xy and 15 ml of DMF was then added with stirring over 30 minutes at 80° C. and further aged for 15 minutes to prepare N-(p-hydroxyphenyl)maleamic acid as a white slurry.

Then, 1.061 g (5.0% by mole per mole of MAN) of stannous oxide was added as the catalyst. The dehydration reaction was carried out under reflux with stirring at about 140° C. for 3 hours. Water generated in the reaction was distilled off as an azeotropic mixture.

After completing the reaction, the solvent was evaporated under reduced pressure and the thus-produced maleimide was extracted from the residue. The same procedure as conducted in Example 1 was repeated except that a mixture of cyclohexane and Xy was used as extraction solvent in place of cyclohexane. The results of the identified product, N-(p-Hydroxyphenyl)-maleimide (abbreviated as MI in Table 4) are shown in Table 4, No. 37.

EXAMPLES 38-41

Substantially the same procedures as employed in Example 37 were carried out except that o-anisidine (Example 38) (abbreviated as MOAN in Table 4), p-chloroaniline (Example 39) (abbreviated as CLAN in Table 4), cyclohexylamine (Example 40) (abbreviated as CHA in Table 4) and dodecylamine (Example 41) (abbreviated as DODA in Table 4) respectively were used in place of PAP, and the catalyst and dehydration time as illustrated in Table 4 were used in the reaction. The corresponding maleamic acids (abbreviated as MA in Table 4) and maleimides (abbreviated as MI in Table 4) could be obtained in all examples. The results are illustrated in Table 4, Nos. 38-41.

EXAMPLES 42-45

Substantially the same procedures as employed in Example 37 were carried out except that p-phenylenediamine (Example 42) (abbreviated as PDA in Table 4), 2,4-tolylenediamine (Example 43) (abbreviated as TDA in Table 4), 4,4'-diamino-diphenylmethane (Example 44) (abbreviated as MDA in Table 4), and 4,4'-diamino-diphenyl ether (Example 45) (abbreviated as DADPE in Table 4) respectively were used in place of PAP in an amount of 0.075 mole in combination with 20 ml of DMF, and the catalyst and dehydration time as illustrated in Table 4 were used in the reaction. The corresponding bismaleimides were obtained. The results are summarized in Table 4, Nos. 42-45.

EXAMPLE 46

A polyamine mixture was used which has a composition represented by the following formula (V):

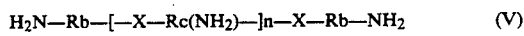

$$H_2N-Rb-[-X-Rc(NH_2)-]n-X-Rb-NH_2 \quad (V)$$

wherein Rb is a phenylene group, Rc is a benzene ring, X is a p-xylylene group; and composed of 78% of 2,2'-bis(p-aminophenyl) xylylendiamine where n is zero, 18.5% of triamine where n is 1, and 6.5% of tetramine and higher amines where n is 2 and more (abbreviated as PAPX in Table 4).

Twenty grams of the polyamine mixture was used in place of PDA and the catalyst and dehydration time as illustrated in Table 4 were used in the reaction. Substantially the same procedures as employed in Example 42 were employed. A polymaleimide (abbreviated as MI in Table 4) corresponding to the polyamine starting material was obtained. The results are illustrated in Table 4, No. 46.

COMPARATIVE EXAMPLES 1-3

The procedure of Example 1 was repeated except without using the catalyst (Comparative Example 1), using 85% ortho-phosphoric acid as the catalyst in an amount of 5% by mole per mole of MAN (Comparative Example 2), or using 96% sulfuric acid as the catalyst in an amount of 5% by mole per mole of MAN (Comparative Example 3). The results are illustrated in Table 5, Nos. 1-3.

The effect of the catalyst in the present invention is clearly evident by comparing the results of the above examples with those of Comparative Example 1 with respect to yield and selectivity of PMI.

When the results of the examples are compared to the results of Comparative Examples 2 and 3, which are representative examples employing known acid catalysts, it is clearly observed that the catalyst of this invention is excellent with respect to the yield and particularly selectivity. In addition, the acid catalysts employed in the comparative examples generate extraordinary large amounts of by-products in the form of extraction residue, compared with the catalysts in the examples.

The catalyst of this invention are stannous oxide, tin salt of the N-substituted maleamic acid or the other tin compound and hence one can omit complex procedures such as washing with water, neutralization, separation and drying which are required for removing an acid catalyst from the reaction mixture. The effect is remarkable in view of practical application.

COMPARATIVE EXAMPLES 4-9

As mentioned above in detail, most of the same metal compounds as those of catalysts usually used for esterification can not be used as catalysts for the reaction of this invention. In order to confirm this, the procedure of Example 1 was repeated except that two nickel compounds (Comparative Examples 4 and 5), a cobalt compound (Comparative Example 6), a copper compound (Comparative Example 7), a magnesium compound (Comparative Example 8) and a manganese compound (Comparative Example 9) as illustrated in Table 5 were used. The results are illustrated in Table 5, Nos. 4-9.

Catalyst activity is not found in any of these comparative examples as clearly shown by comparing these results on the yield and selectivity of PM1 with those of Comparative Example 1 using no catalyst and those of Example 1 using the tin catalyst.

COMPARATIVE EXAMPLES 10 AND 11

The procedure of Example 1 was repeated except that stannic oxide and dibutyl tin dilaurate was respectively used in an amount of 2.5% by mole per mole of MAN in place of SnO. The results are illustrated in Table 5, Nos. 10 and 11.

It is clear that both of oxide and dialkyl compound of tetravalent tin exhibit no effect at all in the reaction.

COMPARATIVE EXAMPLE 12

The procedure of Example 5 was repeated except that stannous sulfate was used in an amount of 2.5% by mole per mole of MAN in place of SnO. The results are illustrated in Table 5, No. 12.

This example suggests that the catalytic activity of the present invention can not be found for a stannous salt of an inorganic strong acid such as sulfuric acid.

TABLE 1

| Example No. | Catalyst | Concentration (mol %/MAN) | Azeotropic solvent | Polar solvent | Starting material Molar ratio (MAN/AN) | Concentration (M/L) | Dehydration (min.) | Purity PMI (%) | Yield PMI (%) | Yield PMA (%) | Selectivity PMI (%) |
|---|---|---|---|---|---|---|---|---|---|---|---|
| 1 | SnO | 2.50 | Xy | DMF | 1.05 | 1.5 | 210 | 98.3 | 88.9 | 7.3 | 96.0 |
| 2 | SnO | 5.00 | Xy | DMF | 1.05 | 1.5 | 150 | 97.0 | 91.2 | 3.5 | 94.5 |
| 3 | SnO | 2.45 | Xy | DMF | 1.02 | 1.5 | 210 | 93.1 | 81.0 | 8.9 | 88.9 |
| 4 | SnO | 1.67 | Xy | DMF | 1.50 | 1.5 | 210 | 93.1 | 94.4 | 3.5 | 97.8 |
| 5 | SnO | 2.38 | Xy | DMF | 1.05 | 2.0 | 210 | 97.7 | 89.3 | 7.0 | 96.0 |
| 6 | SnO | 2.38 | Xy | DMF | 1.05 | 3.0 | 210 | 98.8 | 88.5 | 5.6 | 93.8 |
| 7 | SnO | 2.50 | PhEt | DMF | 1.05 | 1.5 | 210 | 96.6 | 85.0 | 10.0 | 94.5 |
| 8 | SnO | 2.50 | PhCl | DMF | 1.05 | 1.5 | 210 | 99.2 | 90.5 | 4.9 | 95.2 |
| 9 | SnO | 2.50 | Cum | DMF | 1.05 | 1.5 | 180 | 98.5 | 88.0 | 7.2 | 94.8 |
| 10 | SnO | 2.38 | Xy | DMAC | 1.05 | 1.5 | 210 | 94.8 | 90.4 | 5.0 | 95.1 |

TABLE 1-continued

| Example No. | Catalyst | Concentration (mol %/MAN) | Azeotropic solvent | Polar solvent | Starting material Molar ratio (MAN/AN) | Concentration (M/L) | Dehydration (min.) | Purity PMI (%) | Yield PMI (%) | Yield PMA (%) | Selectivity PMI (%) |
|---|---|---|---|---|---|---|---|---|---|---|---|
| 11 | SnO | 2.38 | Xy | DMSO | 1.05 | 1.5 | 210 | 92.8 | 86.0 | 7.0 | 92.5 |
| 12 | SnO | 2.38 | Xy | NMP | 1.05 | 1.5 | 210 | 94.0 | 84.5 | 6.1 | 90.0 |
| 13 | SnO | 3.00 | Xy | DMF | — | 2.0 | 180 | 98.8 | 86.4 | 6.5 | 92.4 |
| 14 | SnO | 4.76 | Xy | DMF | 1.05 | 2.0 | 210 | 99.9 | 95.1 | 3.7 | 98.7 |
| 15 | SnO | 4.76 | Xy | DMAC | 1.05 | 2.0 | 210 | 98.5 | 91.0 | 3.2 | 94.0 |

TABLE 2

| Example No. | Catalyst | Concentration (mol %/MAN) | Azeotropic solvent | Polar solvent | Starting material Molar ratio (MAN/AN) | Concentration (M/L) | Dehydration (min.) | Purity PMI (%) | Yield PMI (%) | Yield PMA (%) | Selectivity PMI (%) |
|---|---|---|---|---|---|---|---|---|---|---|---|
| 16 | Sn(OAc)₂ | 2.50 | Xy | DMF | 1.05 | 1.5 | 210 | 97.1 | 85.9 | 6.9 | 92.3 |
| 17 | Sn(OCOHep)₂ | 2.50 | Xy | DMF | 1.05 | 1.5 | 210 | 93.0 | 86.3 | 8.0 | 93.8 |
| 18 | Sn(OCOPh)₂ | 2.50 | Xy | DMF | 1.05 | 1.5 | 210 | 98.2 | 88.0 | 5.9 | 93.5 |
| 19 | Sn(PMA)₂ | 2.50 | Xy | DMF | 1.05 | 1.5 | 180 | 99.0 | 90.1 | 8.2 | 98.1 |
| 20 | Sn(PMA)₂.DMF | 2.50 | Xy | DMF | 1.05 | 1.5 | 180 | 99.6 | 93.2 | 4.4 | 97.5 |
| 21 | Sn(PMA)₂.TEA | 2.50 | Xy | DMF | 1.05 | 1.5 | 180 | 98.5 | 91.0 | 6.4 | 97.2 |
| 22 | Sn(OAc)₂ | 5.00 | Xy | DMF | 1.02 | 1.5 | 150 | 95.3 | 86.1 | 4.9 | 90.5 |
| 23 | Sn(OCOHep)₂ | 5.00 | Xy | DMF | 1.05 | 2.0 | 120 | 90.1 | 92.3 | 5.7 | 97.9 |
| 24 | Sn(OCOHep)₂ | 5.00 | Xy | DMF | 1.05 | 3.0 | 120 | 86.5 | 91.5 | 3.7 | 95.0 |
| 25 | Sn(OCOHep)₂ | 2.50 | PhEt | DMF | 1.05 | 2.0 | 210 | 91.7 | 82.0 | 13.5 | 94.8 |
| 26 | Sn(OCOHep)₂ | 2.50 | PhCl | DMF | 1.05 | 2.0 | 210 | 93.0 | 87.7 | 7.8 | 95.1 |
| 27 | Sn(OAc)₂ | 2.38 | Xy | DMAC | 1.05 | 2.0 | 210 | 98.5 | 88.1 | 9.6 | 97.5 |
| 28 | Sn(OAc)₂ | 2.38 | Xy | DMSO | 1.05 | 2.0 | 210 | 92.3 | 84.5 | 7.9 | 91.7 |
| 29 | Sn(OAc)₂ | 2.38 | Xy | NMP | 1.05 | 2.0 | 210 | 94.8 | 83.9 | 6.8 | 90.0 |
| 30 | Sn(OAc)₂ | 5.00 | Xy | DMF | 1.05 | 2.0 | 120 | 99.7 | 93.5 | 5.4 | 98.8 |
| 31 | Sn(OAc)₂ | 3.00 | Xy | DMF | — | 2.0 | 210 | 98.5 | 85.0 | 7.1 | 91.5 |

TABLE 3

| Example No. | Catalyst | Concentration (mol %/MAN) | Azeotropic solvent | Polar solvent | Starting material Molar ratio (MAN/AN) | Concentration (M/L) | Dehydration (min.) | Purity PMI (%) | Yield PMI (%) | Yield PMA (%) | Selectivity PMI (%) |
|---|---|---|---|---|---|---|---|---|---|---|---|
| 32 | Sn | 2.50 | Xy | DMF | 1.05 | 2.0 | 240 | 95.0 | 72.5 | 15.2 | 85.5 |
| 33 | SnCl₂ | 2.50 | Xy | DMF | 1.05 | 1.5 | 210 | 95.7 | 70.0 | 16.6 | 83.4 |
| 34 | SnCl₂2H₂O | 2.50 | Xy | DMF | 1.05 | 1.5 | 210 | 94.2 | 68.4 | 17.2 | 82.6 |
| 35 | SnCl₄ | 2.50 | Xy | DMF | 1.05 | 1.5 | 210 | 94.0 | 66.6 | 18.8 | 82.0 |
| 36 | SnCl₄5H₂O | 2.50 | Xy | DMF | 1.05 | 1.5 | 210 | 95.6 | 66.3 | 19.2 | 82.0 |

TABLE 4

| Example No. | Amine starting material | Catalyst | Concentration (mol %/MAN) | Dehydration (min) | Purity MI (%) | Yield MI (%) | Yield MA (%) | Selectivity MI (%) |
|---|---|---|---|---|---|---|---|---|
| 37 | PAP | SnO | 5.0 | 180 | 93.3 | 82.5 | 8.5 | 90.2 |
| 38 | MOAN | SnO | 5.0 | 180 | 98.0 | 85.5 | 8.1 | 93.0 |
| 39 | CLAN | SnO | 5.0 | 210 | 90.2 | 88.0 | 4.9 | 92.5 |
| 40 | CHA | Sn(OAc)₂ | 5.0 | 210 | 89.3 | 80.2 | 7.8 | 87.0 |
| 41 | DODA | Sn(OAc)₂ | 5.0 | 180 | 90.5 | 76.2 | 10.5 | 85.1 |
| 42 | PDA | Sn(OAc)₂ | 3.0 | 210 | 92.0 | 78.7 | 12.8 | 90.3 |
| 43 | TDA | SnO | 5.0 | 210 | 95.5 | 80.5 | 12.5 | 92.0 |
| 44 | MDA | SnO | 3.0 | 180 | 95.0 | 85.0 | 6.8 | 91.2 |
| 45 | DADPE | SnO | 3.0 | 150 | 90.8 | 79.3 | 7.3 | 85.5 |
| 46 | PAPX | SnO | 3.0 | 210 | — | 83.5 | — | — |

Note: MI - N-substituted maleimides, MA - N-substituted maleamic acid

TABLE 5

| Compara. Example | Catalyst | Concentration (mol %/MAN) | Azeotropic solvent | Polar solvent | Starting material Molar ratio (MAN/AN) | Concentration (%) | Dehydration (min) | Purity PMI (%) | Yield PMI (%) | Yield PMA (%) | Selectivity PMI (%) |
|---|---|---|---|---|---|---|---|---|---|---|---|
| 1 | — | 0 | Xy | DMF | 1.05 | 1.5 | 210 | 90.8 | 18.0 | 64.5 | 50.7 |

TABLE 5-continued

| Compara. Example | Catalyst | Concentration (mol %/ MAN) | Azeotropic solvent | Polar solvent | Starting material Molar ratio (MAN/AN) | Starting material Concentration (%) | Dehydration (min.) | Purity PMI (%) | Yield PMI (%) | Yield PMA (%) | Selectivity PMI (%) |
|---|---|---|---|---|---|---|---|---|---|---|---|
| 2 | Orthophosphoric acid (85%) | 5.00 | Xy | DMF | 1.05 | 1.5 | 210 | 85.1 | 39.3 | 45.0 | 71.5 |
| 3 | Sulfuric acid (96%) | 5.00 | Xy | DMF | 1.05 | 1.5 | 120 | 92.6 | 72.9 | 8.4 | 79.6 |
| 4 | Nickel Oxide | 2.50 | Xy | DMF | 1.05 | 1.5 | 210 | 85.5 | 16.0 | 56.3 | 60.6 |
| 5 | Nickel acetate | 2.50 | Xy | DMF | 1.05 | 1.5 | 210 | 87.2 | 17.5 | 67.4 | 65.5 |
| 6 | Cobalt acetate | 2.50 | Xy | DMF | 1.05 | 1.5 | 210 | 88.0 | 16.2 | 78.3 | 74.6 |
| 7 | Copper acetate | 2.50 | Xy | DMF | 1.05 | 1.5 | 210 | 91.3 | 14.0 | 82.5 | 80.0 |
| 8 | Magnesium acetate | 2.50 | Xy | DMF | 1.05 | 1.5 | 210 | 90.8 | 18.8 | 74.1 | 72.8 |
| 9 | Manganese acetate | 2.50 | Xy | DMF | 1.05 | 1.5 | 210 | 88.2 | 15.5 | 67.4 | 47.5 |
| 10 | Stannic oxide | 2.50 | Xy | DMF | 1.05 | 1.5 | 210 | 90.5 | 10.0 | 86.1 | 71.6 |
| 11 | Dibutyl tin dilaurate | 2.50 | Xy | DMF | 1.05 | 1.5 | 210 | 96.8 | 11.8 | 81.9 | 65.0 |
| 12 | Stannous sulfate | 2.50 | Xy | DMF | 1.05 | 2.0 | 210 | 95.5 | 16.9 | 75.6 | 69.2 |

What is claimed is:

1. In a process for the preparation of an N-substituted maleimide by heat-dehydrating an N-substituted maleamic acid in a solvent mixture containing an organic solvent capable of forming water azeotrope and an organic aprotic polar solvent and simultaneously conducting a dehydrating imidization reaction under azeotropic distillation of the reaction generated water, the improvement which comprises conducting the dehydrating imidization in the absence of an acid catalyst and in the presence of one or more catalyst selected from the group consisting of metallic tin, tin oxide, a tin salt of the maleamic acid and a tin compound which forms a tin salt of the maleamic acid in the reaction system.

2. The process of claim 1 wherein the N-substituted maleamic acid is selected from the group consisting of N-methylmaleamic acid, N-butylmaleamic acid, N-octylmaleamic acid, N-dodecylmaleamic acid, N-stearylmaleamic acid, N-cyclohexylmaleamic acid, N-phenylmaleamic acid, N-(o-tolyl)maleamic acid, N-dodecylphenylmaleamic acid, N-chlorophenylmaleamic acid, N-dichlorophenylmaleamic acid, N-(o- or p-hydroxyphenyl)maleamic acid, N-(o- or p-methoxyphenyl)maleamic acid, N-(m-hydroxycarbonylphenyl)maleamic acid and N-(m-nitrophenyl)maleamic acid.

3. The process of claim 1 wherein the N-substituted maleamic acid is selected from the group consisting of N,N'-(m- or p-phenylene)bis-maleamic acid, N,N'-(2,4-tolylene)bis-maleamic acid, N,N'-(4,4'-diphenylmethane)bis-maleamic acid, N,N'-(4,4'-diphenylether)bis-maleamic acid, N,N'-(4,4'-diphenylketone)bis-maleamic acid, N,N'-(4,4'-diphenyldisulfide)bis-maleamic acid, N,N'-(4,4'-diphenylsulfone)bis-maleamic acid, N,N'-(4,4'-p-xylylenediphenyl)bis-maleamic acid and a polymeric homologue thereof.

4. The process of claim 1 wherein the catalyst is metallic tin in powder.

5. The process of claim 1 wherein the catalyst is stannous oxide SnO or tin oxide containing divalent tin atom.

6. The process of claim 1 wherein the catalyst is selected from the group consisting of a tin salt of N-substituted mono-, bis- and poly-maleamic acid and a tin salt adduct obtained by coordinating a neutral ligand or water of crystallization to said tin salt.

7. The process of claim 1 wherein the catalyst is one or more of the tin salt of N-methylmaleamic acid, N-butyl-maleamic acid, N-dodecylmaleamic acid, N-stearylmaleamic acid, N-cyclohexylmaleamic acid, N-phenylmaleamic acid, N-tolylmaleamic acid, N,N'-(m- or p-phenylene)bis-maleamic acid, N,N'-(2,4-tolylene)-bis-maleamic acid, N,N'-(4,4'-diphenylmethane)bis-maleamic acid, N,N'-(4,4'-diphenylether)bis-maleamic acid, N,N'-(4,4'-p-xylylenediphenyl)bis-maleamic acid and a tin salt adduct obtained by coordinating a neutral ligand or water of crystallization to said tin salt.

8. The process of claim 1 wherein catalyst is a tin salt of a weak organic carboxylic acid.

9. The process of claim 8 wherein the tin salt is stannous acetate or stannous 2-ethylhexanoate.

10. The process of claim 1 wherein the catalyst is tin halide.

11. The process of claim 10 wherein the tin halide is stannous chloride or stannic chloride.

12. The process of claim 1 wherein the starting N-substituted maleamic acid is produced in situ without isolation by the reaction of the corresponding maleic anhydride and primary amine.

13. The process of claim 2 wherein N-phenylmaleamicacid is produced in situ without isolation by the reaction of maleic anhydride with aniline.

14. The process of claim 1 wherein the organic solvent capable of forming water azeotrope is one or more of cyclohexane, benzene, toluene, ethylbenzene, xylene, cumene, chlorobenzene, anisole, dichloroethane, diethoxyethane, cyclohexanone, methyl ethyl ketone, methyl i-butyl ketone and trioxane.

15. The process of claim 1 wherein the organic aprotic polar solvent is one or more of dimethylformamide, dimethylacetamide, dimethylsulfoxide, sulfolane, methyl isobutyl ketone, γ-butyrolactone, hexamethylphosphoramide N-methylpyrrolidone, tetramethylurea and 1,3-dimethyl-2-imidazolidinone.

16. The process of claim 1 wherein the organic solvent capable of forming water azeotrope is xylene and the organic aprotic polar solvent is dimethylformamide.

17. The process of claim 1 wherein the concentration of the N-substituted maleamic acid in the reaction system is about 0.1 to 5 moles/l.

18. The process of claim 1 wherein the amount of the catalyst in the reaction system is in the range of 0.001 to 0.2 gram atom as tin per gram mole of the maleamic acid.

19. The process of claim 1 wherein the reaction and/or the purification of the reaction product are conducted in the presence of a polymerization inhibitor.

20. The process of claim 1 wherein N-phenyl maleamic acid is produced without isolation, in the concentration of the 0.5 to 3 mole per liter, by the reaction of maleic anhydride with aniline in the solvent of xylene, and after addition of dimethylforamide, said acid is in situ submitted to dehydration imidization under azeotropic distillation of the reaction generated water in the presence as the catalyst of metallic tin, tin oxide, a tin salt of said acid, a tin compound including stannous acetate, stannous 2-ethylhexanoate, stannous chloride or the mixture thereof in the amount of 0.005 to 0.02 gram atom of tin per mole of said acid, thereby producing N-phenylmaleimide.

* * * * *